United States Patent
Goodall et al.

(10) Patent No.: US 6,629,524 B1
(45) Date of Patent: Oct. 7, 2003

(54) INHALER

(75) Inventors: Stephen F. Goodall, Queensland (AU); James A. H. Graham, Canterbury (AU); Robert W. Geddes, Brisbane (AU)

(73) Assignee: Ponwell Enterprises Limited, Wan Chai (CN)

( * ) Notice: Subject to any disclaimer, the term of this patent is extended or adjusted under 35 U.S.C. 154(b) by 317 days.

(21) Appl. No.: 09/614,196

(22) Filed: Jul. 12, 2000

(51) Int. Cl.[7] .............................................. A61M 11/00
(52) U.S. Cl. ............................ 128/200.14; 128/200.16; 239/338; 239/102.2
(58) Field of Search ...................... 128/200.14, 200.16, 128/200.21, 200.22, 203.23, 204.11, 204.13, 204.14, 204.17, 203.12; 239/338, 102.2

(56) References Cited

U.S. PATENT DOCUMENTS

| 4,558,710 A | 12/1985 | Eichler ........................ 128/720 |
| 4,934,358 A | 6/1990 | Nilsson et al. .......... 128/200.23 |
| 4,976,259 A | 12/1990 | Higson et al. .......... 128/200.18 |
| 5,134,993 A | 8/1992 | van der Linden et al. ....................... 128/200.14 |
| 5,156,776 A | 10/1992 | Loedding et al. ............. 261/27 |
| 5,261,601 A | * 11/1993 | Ross et al. ................ 239/102.2 |

(List continued on next page.)

FOREIGN PATENT DOCUMENTS

| EP | 0234842 | 9/1987 |
| EP | 0432992 | 6/1991 |
| EP | 0542723 | 5/1993 |
| GB | 2272389 | 5/1994 |
| WO | WO 87/04354 | 7/1987 |
| WO | WO89/06147 | 7/1989 |
| WO | WO92/11050 | 7/1992 |
| WO | WO92/15353 | 9/1992 |
| WO | WO93/11866 | 6/1993 |

*Primary Examiner*—Weilun Lo
*Assistant Examiner*—Mital Patel
(74) *Attorney, Agent, or Firm*—Marsh Fischmann & Breyfogle LLP (57) ABSTRACT

An inhaler is disclosed which delivers medicament or other appropriate fluids to a user, typically in droplet form and typically during inhalation. One embodiment of the inhaler includes an inhaler housing, an airflow conduit assembly which at least extends through the inhaler housing, a mouthpiece which is at least fluidly interconnectable with the airflow conduit assembly, a droplet ejection cartridge housing which is at least partially disposed within the airflow conduit assembly, and a droplet ejection cartridge which is removably disposed within the droplet ejection cartridge housing. Dosing of the medicament can be controlled by the measurement of airflow through the device. Droplets of medicament which are discharged by the droplet ejection cartridge are entrained in the flow of air which is drawn through the airflow conduit assembly by the user's inhalation and are discharged from the inhaler through the mouthpiece. The airflow conduit assembly may include a plenum into which air is initially drawn into the airflow conduit assembly, and an airflow conduit which is fluidly interconnected with the plenum for delivering inhaled air to the mouthpiece. The mouthpiece is totally removable from the inhaler and may be detachably interconnectable with the inhaler at two spaced locations. One of these locations corresponds with the mouthpiece being fluidly interconnected with the airflow conduit assembly. The other of these locations is for storage of the mouthpiece after the same is disconnected from the airflow conduit passageway and may include a mouthpiece storage bay with an appropriate cover. A cover may also be provided to seal the relevant portions of the droplet ejection cartridge after disconnection of the mouthpiece from the airflow conduit assembly.

52 Claims, 5 Drawing Sheets

U.S. PATENT DOCUMENTS

| | | | |
|---|---|---|---|
| 5,284,133 A | 2/1994 | Burns et al. | 128/200.23 |
| 5,364,838 A | 11/1994 | Rubsamen | 514/3 |
| 5,392,768 A | 2/1995 | Johansson et al. | 128/200.14 |
| 5,511,726 A | 4/1996 | Greenspan et al. | 239/102.2 |
| 5,694,920 A * | 12/1997 | Abrams et al. | 128/200.16 |
| 5,743,252 A | 4/1998 | Rubsamen et al. | 128/200.14 |
| 5,758,637 A * | 6/1998 | Ivri et al. | 128/200.16 |
| 5,865,185 A | 2/1999 | Collins et al. | 131/194 |
| 5,881,714 A * | 3/1999 | Yokoi et al. | 128/200.14 |
| 5,881,716 A | 3/1999 | Wirch et al. | 128/200.16 |
| 5,894,841 A | 4/1999 | Voges | 128/203.12 |
| 5,906,202 A * | 5/1999 | Schuster et al. | 128/203.23 |
| 5,941,240 A | 8/1999 | Gonda et al. | 128/200.14 |
| 5,943,289 A | 8/1999 | Ahn et al. | 131/328 |
| 5,970,974 A * | 10/1999 | Van Der Linden et al. | 128/200.16 |
| 6,026,809 A | 2/2000 | Abrams et al. | 128/203.15 |
| 6,062,212 A * | 5/2000 | Davison et al. | 128/200.16 |
| 6,085,740 A * | 7/2000 | Ivri et al. | 128/200.16 |
| 6,196,218 B1 | 3/2001 | Voges | 128/200.14 |
| 6,234,167 B1 * | 5/2001 | Cox et al. | 128/200.14 |
| 6,328,033 B1 * | 12/2001 | Avrahami | 128/203.15 |
| 6,402,046 B1 * | 6/2002 | Loser | 239/4 |
| 6,405,934 B1 * | 6/2002 | Hess et al. | 239/4 |

\* cited by examiner

INHALER

FIELD OF THE INVENTION

The present invention generally relates to the field of inhalers for delivering a plurality of droplets of medicament or other appropriate fluids to an individual, typically during inhalation.

BACKGROUND OF THE INVENTION

Many types of medicaments or other types of fluids are delivered by inhalation for treating/addressing various types of conditions. Three general types of inhalers may be used for this type of "respiratory therapy." Metered dose inhalers ("MDIs") are relatively small, portable units which have a medicament disposed within a container of a pressurized gas or propellant (e.g., a mixture of medicament and propellant). The patient typically pushes down on this container to direct a "burst" of a mixture of propellant and medicament into the patient's mouth during inhalation, with the propellant "burst" being provided by the pressure within the container. A fixed number of doses are available in a given MDI. What all the medicament has been dispensed from the container, typically the MDI or at least the container of medicament/propellant is discarded.

Another categorical type of inhaler is a nebulizer. These types of inhalers are not as portable as an MDI, and are more commonly used in a clinic or hospital setting. Generally, a nebulizer houses an appropriate medicament in liquid form. Gas from an external source is directed through an appropriate line under pressure and into the nebulizer to aerosolize the medicament for transport to the patient for delivery by inhalation. At the end of the treatment or upon the consumption of all of the liquid medicament in the nebulizer, and typically after a sterilization procedure, additional liquid medicament may be poured into the nebulizer for subsequent treatments.

The third general type of inhaler has a degree of portability which is similar to that of the MDI, but which uses sources other than an external supply of pressurized gas to generate droplets of the desired medicament. Some inhalers of this type use a small "on-board" source of pressurized gas to aerosolize a liquid medicament. Other inhalers use piezo-electric crystals and the like to aerosolize a liquid medicament in some manner. U.S. Pat. No. 5,894,841 to Voges, entitled "Dispenser," discloses another inhaler of this general categorical type, but which uses a "droplet on demand" ejection device to generate droplets of medicament in the desired manner (e.g., a piezoelectric device of the kind used in ink jet printing or a thermal "bubble jet" device of the kind used in inkjet printing). The cartridge of medicament in the inhaler from U.S. Pat. No. 5,894,841 may be replaced after its medicament has been consumed or spent.

BRIEF SUMMARY OF THE INVENTION

The present invention generally relates to enhancing one or more aspects associated with the delivery of medicament or other appropriate fluids/substances in typically the form of a plurality of droplets/particles for inhalation by a user of an inhaler (hereafter "medicament").

A first aspect of the present invention is generally directed to an inhaler which includes an inhaler housing. At least one airflow passageway is interconnected with the inhaler housing. One or more portions of the airflow passageway(s) may extend beyond the inhaler housing, while other portions thereof may extend through the inhaler housing. In any case, there is at least one air inlet port for drawing air into the airflow passageway(s) utilized by the inhaler. Medicament is directed into this airflow passageway(s) by a droplet ejection cartridge. This droplet ejection cartridge includes a medicament reservoir, a plurality of droplet ejection orifices, and at least one droplet ejection actuator. Medicament from the reservoir is made available for ejection out through one or more of the droplet ejection orifices by activation of the droplet ejection actuator(s). In one embodiment there is a separately operable droplet ejection actuator for each droplet ejection orifice such that droplets of medicament may be directed out of the desired droplet ejection orifice(s). In any case, droplets of medicament which are entrained in the airflow through the airflow passageway(s) are directed into a mouthpiece when the same is appropriately interconnected with the airflow passageway(s). Therefore, a user simply positions his/her mouth about the mouthpiece and inhales for respiratory delivery of medicament by the inhaler.

The droplet ejection cartridge of the subject first aspect is removably disposed within a droplet ejection cartridge housing. In this regard, the droplet ejection cartridge housing includes a second droplet ejection cartridge aperture into which the droplet ejection cartridge may be positioned for support by the droplet ejection cartridge housing. Desirably, the second droplet ejection cartridge aperture of the droplet ejection cartridge housing is aligned with a first droplet ejection cartridge aperture which is formed in the inhaler housing. Therefore, the droplet ejection cartridge may be both loaded into and removed from the second droplet ejection cartridge aperture of the droplet ejection cartridge housing by passage through the first droplet ejection cartridge aperture of the inhaler housing. The droplet ejection cartridge housing also includes a droplet ejection aperture through which droplets are directed by the plurality of droplet ejection orifices at the desired time.

Various refinements exist of the features noted in relation to the subject first aspect of the present invention. Further features may also be incorporated in the subject first aspect of the present invention as well. These refinements and additional features may exist individually or in any combination. For instance, an appropriately configured cover may be provided for the first droplet ejection cartridge aperture formed in the inhaler housing and through which the droplet ejection cartridge may be directed for loading/unloading of the same from the droplet ejection cartridge housing. This cover may be movably interconnected with the inhaler housing, such as by a slide interface, a hinged interconnection, or the like. This particular cover may also be totally removable from the inhaler housing and may detachably interface with the inhaler housing (e.g., via a the snaplock type interconnect).

The inhaler of the subject first aspect of the present invention may also include an airflow conduit assembly which is interconnected with the inhaler housing. Each airflow passageway utilized by the inhaler of the subject first aspect may be directed through this airflow conduit assembly. Fluid interconnection between this airflow conduit assembly and the mouthpiece may be provided by engaging an inlet end of the mouthpiece on an outlet end of the airflow conduit assembly.

The droplet ejection cartridge housing may be disposed within the above-noted airflow conduit assembly and retained therein such that the droplet ejection cartridge housing and interior of the airflow conduit assembly are maintained in spaced relation so as to define at least part of the noted airflow passageway(s). One way in which this may be affected is by providing a pair of spaced apart partitions of sorts which extend between the interior surface of the airflow conduit assembly and the droplet ejection cartridge housing such that airflow is directed therebetween. In one embodiment, the droplet ejection cartridge housing includes first and second sides which are disposed opposite of each other, and further includes third and fourth sides which are disposed opposite of each other. One pair of the above-noted partitions may extend between the interior surface of the airflow conduit assembly and the first side of the droplet ejection cartridge housing to define one airflow passageway around the droplet ejection cartridge housing. Another pair of the above-noted partitions may extend between the interior surface of the airflow conduit assembly and the second side of the droplet ejection cartridge housing to define another airflow passageway around the droplet ejection cartridge housing. In one embodiment there is no airflow passageway between the interior of the airflow conduit assembly and either the third or fourth sides of the droplet ejection cartridge housing. Therefore, this then allows for a first airflow passageway section to be directed toward the droplet ejection cartridge housing, and then to effectively "split" the same so as to flow around the droplet ejection cartridge housing on only two of the opposing sides of the droplet ejection cartridge housing.

The above-noted airflow conduit assembly may include both a plenum and an airflow conduit. One end of the airflow conduit could interface with the plenum, while its opposite end could interface with the mouthpiece. The first inlet port may be on the plenum. The size of this first inlet port may be adjustable, such as by including a cover or the like which is movably interconnected with the inhaler housing. Modification of the size of the first inlet port by moving the cover relative to the inhaler housing in turn modifies the inhalation resistance provided by the inhaler of the subject first aspect (e.g., for user preference and/or comfort). The first inlet port also may be offset in relation to the end of the airflow conduit which interfaces with the plenum. That is, the first inlet port on the plenum and the airflow conduit may be out of alignment such that air will not flow through the first inlet port on the plenum, through the plenum, and to the airflow conduit along a linear path. The plenum may be utilized to reduce the turbulence of air drawn therein prior to directing the same through the airflow conduit for injection of medicament droplets therein. Consider the case where the airflow conduit extends at least generally along a reference axis between its pair of opposing ends. In one embodiment, an area which is occupied by the plenum within a reference plane which is perpendicular to the reference axis along which the airflow conduit extends, is greater than an area occupied by the "plenum end" of the airflow conduit within a reference plane which is also perpendicular to the reference axis along which the airflow conduit extends.

Various portions of the airflow conduit assembly may be sized/contoured to facilitate the flow of air therethrough in a desired manner, as well as to provide a mechanism for the estimation of the rate of airflow through the conduit, all in relation to the subject first aspect of the present invention. Consider the case where the airflow conduit assembly includes an airflow conduit having 1U an inlet port and an outlet port which are longitudinally spaced relative to a reference axis along which the airflow conduit at least generally extends. Consider as well that there are at least three locations along this reference axis which have different diameters (i.e., the diameter of the airflow conduit may vary along its longitudinal extent). These three locations may be characterized as first, second, and third locations progressing in a direction corresponding with the airflow through the airflow conduit during inhalation (i.e., in a direction from the inlet port of the airflow conduit to the outlet port of the airflow conduit). The first location may actually define the first inlet port. The first, second, and third, which again represent different longitudinal positions along the noted airflow conduit, have first, second, and third diameters, respectively. The first diameter at the first longitudinal location is greater than the second diameter of the second longitudinal location. This change in diameter may be utilized to provide an increase in air velocity and consequently a reduction in pressure. The third diameter at the third longitudinal location is greater than the second diameter at the second longitudinal location. The droplet ejection cartridge housing may be disposed within a portion of the airflow conduit assembly which is defined by this third diameter such that the airflow through the airflow conduit may be directed "around" the droplet ejection cartridge housing.

Further enhancements may be incorporated into the design of the inhaler of the subject first aspect in relation to the manner of ejecting medicament droplets into the airflow. In this regard, the droplet ejection cartridge housing may include a first end which projects at least generally toward the mouthpiece when the same is fluidly interconnected with the airflow passageway(s) associated with the inhaler. This first end of the droplet ejection cartridge may include a recess having the above-noted droplet ejection aperture formed therein. The droplet ejection cartridge may be oriented in the droplet ejection cartridge housing such that the plurality of droplet ejection orifices direct medicament droplets from the droplet ejection cartridge out through the droplet ejection aperture which is recessed on the first end of the droplet ejection cartridge housing. Recessing the droplet ejection discharge aperture in this manner is believed to introduce the medicament droplets into a zone having a minimal airflow therethrough. Vanes may be attached to the first end of the droplet ejection cartridge housing to further shield the ejected medicament droplets from the airflow which is passing the droplet ejection cartridge housing.

The mouthpiece of the subject first aspect of the present invention is at least fluidly interconnectable with the above-noted airflow passageway. Various features may be incorporated in the subject first aspect in relation to this mouthpiece. The length of the mouthpiece may be selected such that medicament that is ejected from the droplet ejection cartridge is traveling at least at substantially the same, and more preferably the same, velocity as the airflow prior to exiting an outlet end of the mouthpiece. In the case where the airflow passageway(s) is defined by an airflow conduit assembly, an inlet end of the mouthpiece may interface with the outlet end of the airflow conduit assembly. An outlet end of the mouthpiece, which is disposed opposite the inlet end of the mouthpiece, would then typically be inserted into the user's mouth. In one embodiment, the inlet end of the mouthpiece has a circular cross-sectional profile, while the outlet end of the mouthpiece has an elliptical cross-sectional profile of a horizontal axis making it similar to the shape of the mouth of a user (e.g., a major axis that is at least substantially co-linear with the "line" between the user's upper and lower lips when joined). Having an elliptical cross-sectional profile of the outlet end of the mouthpiece also allows the same to be orientated such that it is at least generally aligned with a perimeter of the plurality of droplet ejection orifices of the droplet ejection cartridge. to Different sizes may also be utilized for the inlet and outlet ends of the mouthpiece. An area of the opening defined by the inlet end of the mouthpiece may be larger than an area of the opening defined by the outlet for reducing the turbulence of the airflow entering the mouthpiece.

Another feature which may be utilized in relation to the mouthpiece of the subject first aspect is that it may be totally removable from the inhaler, and may interface or be interconnected with the inhaler at two different, spaced locations. When interconnected with the inhaler at a first location, the mouthpiece is fluidly interconnected with the airflow passageway(s) for purposes of delivering medicament droplets to a user of the inhaler. Disconnecting the mouthpiece from the airflow passageway(s) allows the mouthpiece to be moved to its second location on the inhaler, such as for storage purposes. In one embodiment the second location is a mouthpiece storage bay within the inhaler housing in which the mouthpiece may be positioned. The mouthpiece may be enclosed within the storage bay by including a mouthpiece storage bay cover which is at least partially detachably interconnectable with the inhaler housing for accessing the mouthpiece storage bay (e.g., using a slidable interconnection, using a hinge assembly, having the cover be totally removable from the inhaler housing). Removal of the fluid interconnection between the mouthpiece and airflow passageway(s) may expose the plurality of droplet ejection orifices to ambient conditions. It may be desirable to provide a droplet ejection orifice cover with a seal which may be disposed within the opening which remains after the mouthpiece is removed such that the seal may be disposed about the plurality of droplet ejection orifices. This droplet ejection orifice cover may be interconnected with the inhaler housing by a tether, although other ways may be utilized for storing the droplet ejection orifice cover when not in use.

A second aspect of the present invention is generally directed to an inhaler which includes an inhaler housing. At least one airflow passageway is interconnected with the inhaler housing. One or more portions of the airflow passageway(s) may extend beyond the inhaler housing, while other portions thereof may extend through the inhaler housing. In any case, there is at least one inlet port to the airflow passageway(s) utilized by the inhaler. Medicament from an appropriate container, which is interconnected with the inhaler housing, is directed into this airflow passageway (s) by a droplet ejection device. Medicament droplets are entrained within the airflow through the airflow passageway (s) and are directed into the mouth of a user of the inhaler through a mouthpiece which is at least fluidly interconnectable with the airflow passageway(s) or a first location on the inhaler. The mouthpiece may also be fluidly disconnected from the airflow passageway(s), totally removed from contact with the inhaler, and then interconnected with the inhaler at a second location which is spaced from the first location. When interconnected with the inhaler at the first location, the mouthpiece is fluidly interconnected with the airflow passageway(s) for purposes of delivering medicament droplets to a user of the inhaler. Separating the mouthpiece from the airflow passageway(s) allows the mouthpiece to be moved to its second location on the inhaler, such as for storage purposes. In one embodiment the second location is a mouthpiece storage bay within the inhaler housing in which the mouthpiece may be positioned. The mouthpiece may be enclosed within the storage bay by including a mouthpiece storage bay cover which is at least partially detachably interconnectable with the inhaler housing for accessing the mouthpiece storage bay (e.g., using a slidable interconnection, using a hinge assembly, having the cover be totally removable from the inhaler housing). Removal of the fluid interconnection between the mouthpiece and airflow passageway(s) may expose the plurality of droplet ejection orifices to ambient conditions. It may be desirable to provide a droplet ejection orifice cover with a seal which may be disposed within the opening which remains after the mouthpiece is removed such that the seal may be disposed about the plurality of droplet ejection orifices. This droplet ejection orifice cover may be interconnected with the inhaler housing by a tether, although other ways may be utilized for storing the droplet ejection orifice cover when not in use.

All of the various other features addressed above in relation to the first aspect of the present invention may be used individually and/or in any combination in relation to this second aspect of the present invention as well.

A third aspect of the present invention is an inhaler which includes a plenum with an air inlet port. An airflow conduit is fluidly interconnected with this plenum and includes a pair of longitudinally spaced ends. One of these ends interfaces with the plenum, while its opposite end interfaces with a mouthpiece. There is an offset between the air inlet port on the plenum and the end of the airflow conduit which interfaces with the plenum. A droplet ejection device is at least fluidly interconnectable with the airflow conduit. Medicament droplets which are entrained in the airflow through the airflow conduit, from the plenum, are directed into a mouth of a user of the inhaler through the mouthpiece.

All of the various other features addressed above in relation to the first aspect of the present invention may be used individually and/or in any combination in relation to this second aspect of the present invention as well.

BRIEF DESCRIPTION OF THE SEVERAL VIEWS OF THE DRAWING

FIG. 1 is a perspective view of one embodiment of inhaler in a storage/transport configuration.

FIG. 2 is a perspective view of the inhaler of FIG. 1 in a medicament delivery configuration.

FIG. 3 is an exploded, perspective view of the inhaler of FIG. 1.

FIG. 4 is an exploded, perspective view of an airflow conduit assembly utilized by the inhaler of FIG. 1, including other components which interface with the airflow conduit assembly.

FIG. 5 is a cutaway, side view of the airflow conduit assembly of FIG. 4 taken along its longitudinal extent.

FIG. 6 is a front view of the droplet ejection cartridge housing of FIG. 4 when the same is disposed in the assembled airflow conduit assembly of FIG. 4 and with the droplet ejection cartridge of FIG. 2 being disposed in the droplet ejection cartridge housing.

FIG. 7 is a cross-sectional view of a forward portion of the droplet ejection cartridge housing of FIG. 4 with the droplet ejection cartridge of FIG. 2 disposed therein.

FIG. 8 is a plan view of a droplet ejection orifice cover utilized by the inhaler of FIG. 1.

DETAILED DESCRIPTION OF THE INVENTION

The present invention will now be described in relation to the accompanying drawings which at least assist in illustrating its various pertinent features. One embodiment of an inhaler 2 is presented in FIGS. 1–4 for delivering medicament to a user during inhalation. The inhaler 2 generally includes an inhaler housing 6. At least part of an airflow conduit assembly 52 is disposed within and extends at least generally along the length or longitudinal extent of the inhaler housing 6. The primary function of the airflow conduit assembly 52 is to provide a flowpath for air inhaled by a user of the inhaler 2. Another component of the inhaler 2 is a droplet ejection cartridge housing 104 which is at least partially disposed within the airflow conduit assembly 52. Disposed within the droplet ejection cartridge housing 104 is a droplet ejection cartridge 152. Medicament or other appropriate fluids are ejected or discharged from the droplet ejection cartridge 152 into the airflow conduit assembly 52, typically during inhalation by a user of the inhaler 2 and typically in the form of a plurality of droplets, which are then entrained in the flow of air being inhaled by the user of the inhaler 2. This airflow with entrained droplets is then directed into the user's mouth through a mouthpiece 200 which is detachably interconnected with the airflow conduit assembly 52, and thereby in fluid communication therewith. The inhaler 2 also preferably includes an appropriate user interface 38. The user interface 38 may include a liquid crystal display screen or the like for various purposes, such as to advise and inform the user of relevant dose information (e.g., current inhaler status, past activity, programmed dosage). The user interface 38 may also include a key pad or other data entry device to allow interrogation of the inhaler 2 by the user or prescribing physician, as well as to provide other desired functionality.

The inhaler housing 6 defines the "packaging" of sorts for the inhaler 2. Generally, the inhaler housing 6 includes a rear end 7 and a front end 8. The distance between the rear end 7 and the front end 8 of the inhaler housing 6 defines a length dimension or longitudinal extent for the inhaler housing 6. Part of the airflow conduit assembly 52 extends beyond the rear end 7 the inhaler housing 6 and is where air is initially drawn into the airflow conduit assembly 52. The mouthpiece 200 extends beyond the front end 8 of the inhaler housing 6 when the mouthpiece 200 is fluidly interconnected with the airflow conduit assembly 52, and is where the air with the entrained medicament droplets exit the inhaler 2 for delivery into the mouth of a user of the inhaler 2 (FIG. 2). In this regard, the front end 8 of the inhaler 2 includes an exit aperture 42 through which the mouthpiece 200 extends to appropriately interface and fluidly interconnect with the airflow conduit assembly 52. When the mouthpiece 200 is disconnected from the airflow conduit assembly 52 (FIGS. 1 and 3), a droplet ejection orifice cover 20 is preferably disposed over the entirety of the exit aperture 42 and seals against relevant portions of the droplet ejection cartridge 152 as will be discussed in more detail below. The droplet ejection cartridge 152 again is disposed in the droplet ejection cartridge housing 104, which in turn is disposed on an end of the airflow conduit assembly 52 which is at least generally proximate the front end 8 of the inhaler housing 6.

Disconnection of the mouthpiece 200 from the airflow conduit assembly 52 may provide a number of advantages. Modification of the configuration of the inhaler 2 from that presented in FIG. 2 to that presented in FIG. 1 may allow for more effective transport and/or storage of the inhaler 2 during periods of non-use. Removal of the mouthpiece 200 from its fluid interconnection with the airflow conduit assembly 52 may also be utilized to preclude any delivery of medicament from the inhaler 2 (e.g., the inhaler 2 may be configured such that it will not be operable without the mouthpiece 200 being attached to the airflow conduit assembly 52). In any case, the inhaler housing 6 includes a mouthpiece storage bay 14 for receiving and storing the mouthpiece 200 when the same is not fluidly interconnected with the airflow conduit assembly 52 by initially totally disconnecting the mouthpiece 200 from the inhaler 2. That is, even when the mouthpiece 200 is fluidly disconnected from the airflow conduit assembly 52 by a total separation from the inhaler 2, thereafter it may be re-interconnected with the inhaler 2, albeit at another location which is spaced from that where the mouthpiece 200 interfaces with the airflow conduit assembly 152.

Preferably the mouthpiece 200 is at least somewhat protected from at least certain types of contamination at times when the inhaler 2 is not configured for medicament delivery. In this regard, a mouthpiece storage bay cover 10 interfaces with the inhaler housing 6 in such a manner that the mouthpiece storage bay cover 10 may be moved relative to the inhaler housing 6 to expose the mouthpiece storage bay 14 for transfer of the mouthpiece 200 into/out of the mouthpiece storage bay 14. The mouthpiece storage bay cover 10 may also be positioned relative to the inhaler housing 6 to retain the mouthpiece 200 within the inhaler housing 6 by defining an at least partially enclosed, and more preferably a totally enclosed, storage space. Enclosure of the mouthpiece 200 within the mouthpiece storage bay 14 offers a degree of protection from exposure of the mouthpiece 200 to at least certain types of contaminants when the inhaler 2 is not in use. A snap-lock interconnection could be also utilized within the mouthpiece storage bay 14 to further secure the position of the mouthpiece 200 relative to the inhaler housing 6 (not shown). Notwithstanding the benefits of providing an enclosed space for storage of the mouthpiece 200 when not in use for medicament delivery operations, the provision of two separate and discrete positions for the mouthpiece 200 on the inhaler 2 may be provided without a requirement for an enclosed storage space. For instance, a snap-lock interconnection or the like on an exterior of the inhaler housing 6 could also be provided at a location which is displaced from that where the mouthpiece 200 fluidly interfaces with the airflow conduit assembly 52 (not shown) for storage of the mouthpiece 200 during periods of nonuse of the inhaler 2 by initially totally separating the mouthpiece 200 from the inhaler 2.

In the illustrated embodiment, the mouthpiece storage bay cover 10 is slidably interconnected with the inhaler housing 6 such that the cover 10 may be moved relative to the inhaler housing 6 and yet remain interconnected therewith. Other ways of mounting the cover 10 on the inhaler housing 6 may be utilized to achieve the desired relative movement to access the mouthpiece storage bay 14 while still remaining interconnected with the inhaler housing 6, such as a hinge system or the like (not shown). Moreover, the mouthpiece storage bay cover 10 could be totally removable from the inhaler housing 6 through use of an appropriate detachable interconnection mechanism. The inhaler housing 6 also includes a cartridge aperture 16. The droplet ejection cartridge 152 of FIG. 2 may be directed through the cartridge aperture 16 of the inhaler housing 6 to both install and remove the droplet ejection cartridge 152 from the droplet ejection cartridge housing 104. Once again, the droplet ejection cartridge 152 is at least partially disposed within the airflow conduit assembly 52, which is in turn at least partially enclosed within the inhaler housing 6. The inhaler 2 further includes a cartridge access cover 18 to open/close the cartridge aperture 16 at the desired time by a relative movement between the cover 18 and the inhaler housing 6. In the illustrated embodiment, the cartridge access cover 18 is totally removable from the inhaler housing 6. However, the cartridge access cover 18 could also be interconnected with the inhaler housing 6 in the various ways discussed above in relation to the mouthpiece storage bay cover 10 for providing access to the cartridge aperture 16.

The airflow conduit assembly 52 is interconnected with and at least partially enclosed within the inhaler housing 6. Reference should now be made to FIGS. 1–5. There are two main components of the airflow conduit assembly 52. A plenum 56 is disposed beyond the rear end 7 of the inhaler housing 6. One way to construct the plenum 56 is by having an upper plenum section 56a and a lower plenum section 56b which are appropriately interconnected (e.g., detachably via one or more appropriate fasteners). Integral construction techniques could also be utilized for the plenum 56 (e.g., by forming the same from a single piece of material such that there is no joint therein). In any case, air is initially drawn into the airflow conduit assembly 52 through an air inlet 60 which extends through an end wall 57a of the plenum 56. This air inlet 60 is offset from the airflow conduit 68 which extends at least generally along a reference axis 74. Terms such as "longitudinal" or the like herein refer at least generally to a direction which is at least parallel with the reference axis 74, while terms such as "lateral" or the like herein refer at least generally to a direction which is at least generally perpendicular to the reference axis 74. Therefore, the air inlet 60 may also be characterized as being laterally spaced from the end of the airflow conduit 68 which interfaces with the plenum 56.

Figure 1:
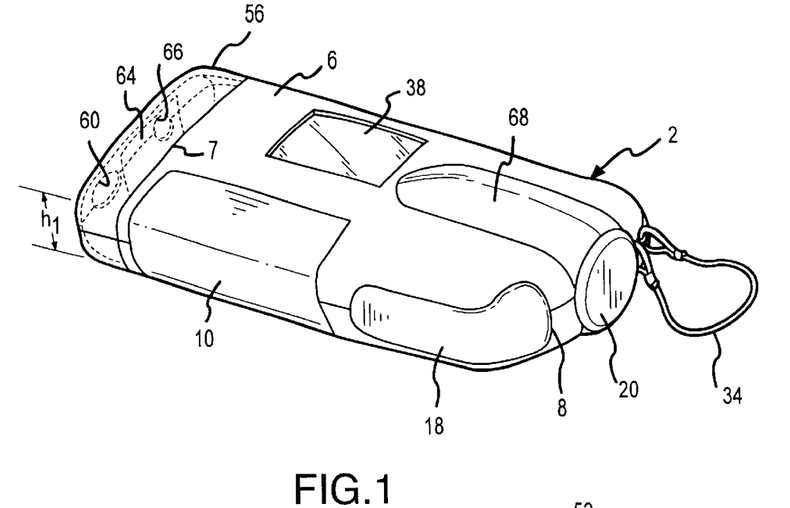
Figure 2:
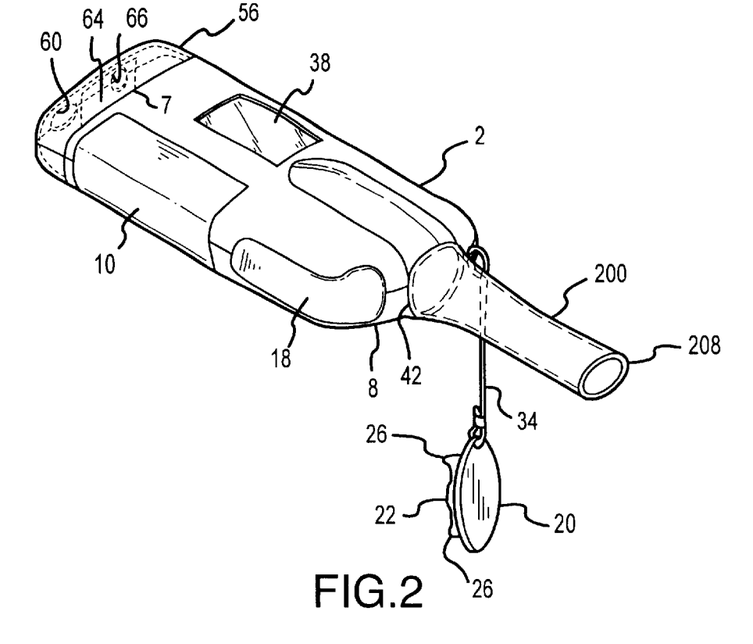
Figure 3:
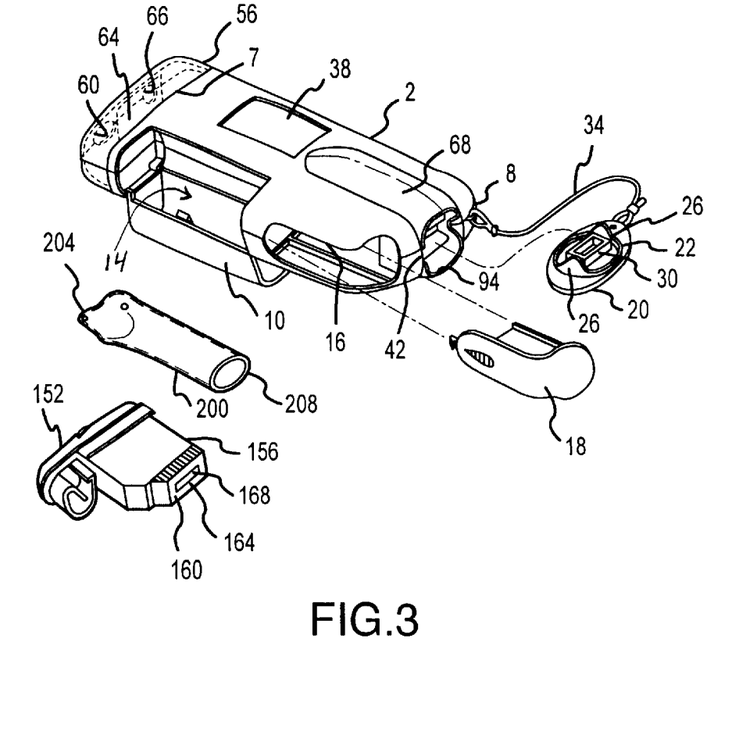
Figure 5:
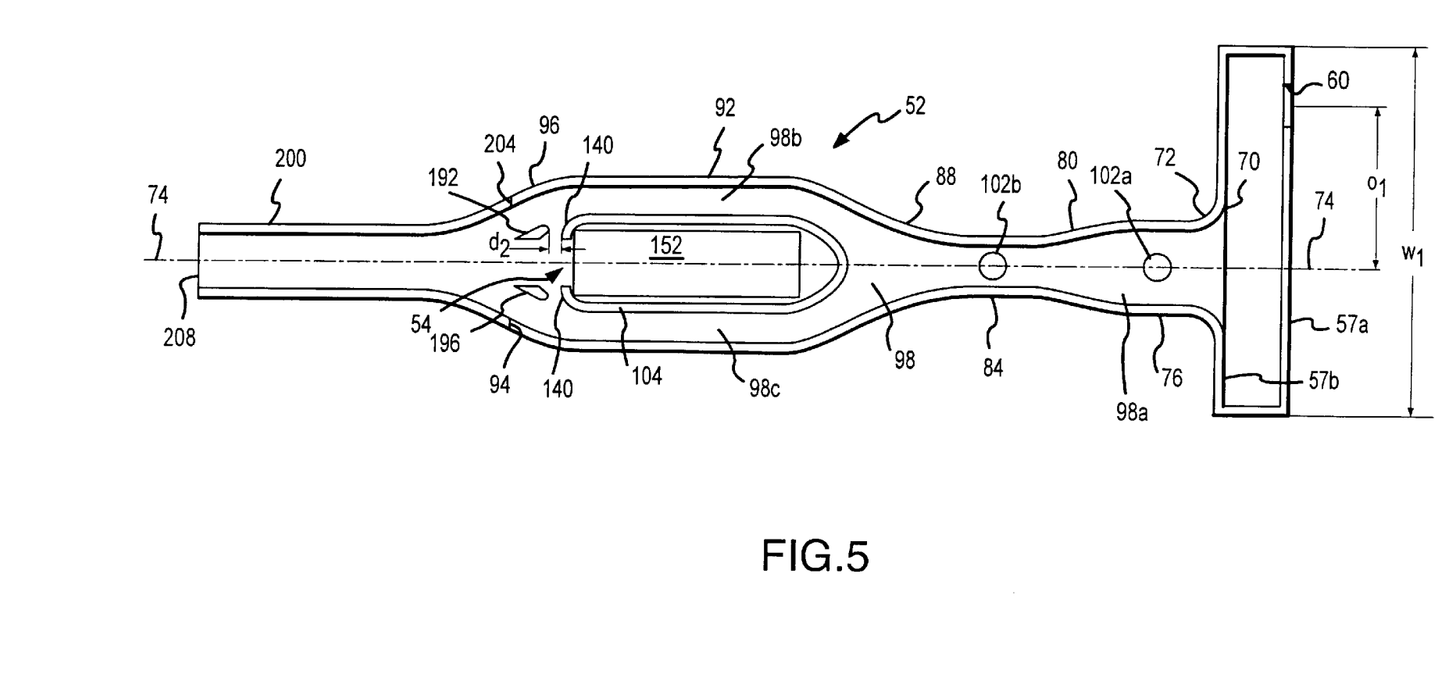

Airflow into the plenum 56 through the air inlet 60 may be regulated by a gate 64 which is movably interconnected with the end wall 57a of the plenum 56 (e.g., via a slidable interconnection). A finger grip 66 or the like may be provided on the gate 64 to facilitate engagement/movement thereof by a user of the inhaler 2. Modifying the amount of the air inlet 60 on the plenum 56 which is exposed, by movement of the gate 64 relative to the plenum 56, modifies the airflow characteristics into the plenum 56. In one embodiment, the plenum 56 has one or more of the following characteristics: 1) the volume of the plenum 56 is at least about 9,000 mm$^2$; 2) the lateral extent of the plenum 56, represented by the dimension "$w_1$" in FIG. 5, is at least about 40 mm; 3) the height or depth of the plenum 56, represented by the dimension "$h_1$" in FIG. 1, is about 15 mm; 4) the longitudinal extent of the plenum 56, or the distance between the end wall 57a and an opposing end wall 57b of the plenum 56 with which the airflow conduit 68 interfaces with the plenum 56 is at least about 15 mm as measured along or parallel to the axis reference 74; and 5) the center of the air inlet 60 is offset or laterally spaced from the center of the airflow conduit 68, represented by the dimension "$o_1$" presented in FIG. 5, by a distance of at least about 20 mm.

The airflow conduit 68 is fluidly interconnected with the plenum 56 and extends at least generally along the reference axis 74 between the rear end 7 of the inhaler housing 6 and its front end 8 as noted. Note that the forward portion of the airflow conduit 68 is not totally enclosed by the inhaler housing 6. The rear end 7 and the front end 8 of the inhaler housing 6 are spaced along the reference axis 74, and thereby may be characterized as being longitudinally spaced. One way to construct the airflow conduit 68 is by having an upper airflow conduit section 68a and a lower airflow conduit section 68b which are reliably sealed along adjoining surfaces and appropriately interconnected (e.g., detachably via one or more appropriate fasteners). Integral construction techniques can also be utilized for the airflow conduit 68 as well (e.g., forming the airflow conduit 68 from a single piece of material such that there is no joint of any kind therein). Preferably, the upper plenum section 56a and upper airflow conduit section 68a are integrally formed, and the lower plenum section 56b and lower airflow conduit section 68b are integrally formed such that these upper and lower "subassemblies" of sorts may be detachably interconnected by a plurality of appropriate fasteners as evident by a review of FIG. 4.

One end of the airflow conduit 68 is defined by an inlet port 70 which interfaces with the above-described plenum 56 of the airflow conduit assembly 52. Another end of the airflow conduit 68 is defined by an outlet port 94 which interfaces with the mouthpiece 200 when the same is fluidly interconnected with the airflow conduit assembly 52 for medicament delivery operations. The configuration of the airflow conduit 68 facilitates the disposition of the droplet ejection cartridge 152 at least partially there within (as well as the droplet ejection cartridge housing 104) and the realization of desired airflow characteristics. In this regard, the airflow conduit 68 includes a first section 72 which at least generally diverges away from the reference axis 74 progressing in the direction of the inlet port 70 of the airflow conduit 68. This divergent configuration may be realized by having a wall of the airflow conduit 68 which defines the first section 72 be at least generally accurately-shaped to measure the rate of airflow through the airflow conduit 68 from the plenum 56 during inhalation by a user of the inhaler 2. In one embodiment, the first section 72 of the airflow conduit 68 has one or more of the following characteristics: 1) the diameter of the inlet port 70 on the end of the first section 72 is within a range of about 28 mm to about 40 mm; and 2) the wall of the first section 72 is entirely defined by a radius which is within a range of about 14 mm to about 20 mm.

A second section 76 of the airflow conduit 68 extends from an end of the first section 72 toward the outlet port 94 of the airflow conduit 68. The principal function of the second section 76 is to align the incoming flow so the flow is parallel at the longitudinal position corresponding with a pressure sensor 102a. The pressure sensor 102a interfaces with the second section 76 at one of the pressure sensor ports 5 (both ports being collectively defined by port sections 58a on the upper airflow conduit section 68a, and a corresponding port section 58b on the lower airflow conduit section 68b) on the airflow conduit 68 (FIG. 4) for purposes of generating an electrical signal which is representative of at least one inhalation characteristic for purposes of controlling the operation of the inhaler 2. In one embodiment, the second section 76 of the airflow conduit 68 has one or more of the following characteristics: 1) the second section 76 is at least generally cylindrical and concentrically disposed about the reference axis 74; 2) the diameter of the second section 76 is within a range of about 14 mm to about 20 mm; 3) the length of the second section 76, measured along the reference axis 74, is within a range of about 14 mm to about 20 mm; and 4) the pressure sensor 102a is positioned at least substantially midway, and more preferably midway, along the second section 76.

A third section 80 of the airflow conduit 68 extends from an end of the second section 76 toward the outlet port 94 of the airflow conduit 68. The principal function of the third section 80 is to provide and transition to the venturi throat which is defined by a fourth section 84 of the airflow conduit 68. Generally, the third section 80 at least generally converges toward the reference axis 74 progressing in the direction of the outlet port 94 of the airflow conduit 68.

A fourth section 84 of the airflow conduit 68 extends from an end of the third section 80 toward the outlet port 94 of the airflow conduit 68. The principal function of the fourth section 84 is to induce a lower pressure than at second section 76 as so indicate the airflow through the airflow conduit 68. Another pressure sensor **102*b* interfaces with the fourth section 84 at another of the pressure sensor ports 5 (both ports again being collectively defined by port sections 58*a* on the upper airflow conduit section 68*a*, and a corresponding port section 58b on the lower airflow conduit section 68*b*) on the airflow conduit 68 (FIG. 4) for purposes of generating an electrical signal which is representative of at least one inhalation characteristic for purposes of controlling the operation of the inhaler 2. In one embodiment, the fourth section 84 of the airflow conduit 68 has one or more of the following characteristics: 1) the fourth section 84 is at least generally cylindrical and concentrically disposed about the reference axis 74; 2) the diameter of the fourth section 84 is within a range of about 7 mm to about 10 mm; 3) the length of the fourth section 84, measured along the reference axis 74, is within a range of about 7 mm to about 10 mm; and 4) the transition radius on each end of the fourth section 84** is within a range of about 20 mm to about 40 mm.

Two pressure sensors 102 are utilized by the embodiment of the inhaler 2 presented herein. However, it may be possible to use a single pressure sensor (not shown). In this case, it may not be necessary to include the above-described third section 80 and fourth section 84 for the airflow conduit 68. That is, the second section 76 of the airflow conduit 68 may then directly interface with a fifth section 88 of the airflow conduit 68. In this regard, the fifth section 88 of the airflow conduit 68 extends from an end of the fourth section 84 toward the outlet port 94 of the airflow conduit 68. The principal function of the fifth section 88 is to reduce flow velocities to suit mixing with the medicament when dispensed into the airflow conduit 68 by the droplet ejection cartridge 152. Generally, the fifth section 88 at least generally diverges away the reference axis 74 progressing in the direction of the outlet port 94 of the airflow conduit 68. In one embodiment, the fifth section 88 of the airflow conduit 68 has one or more of the following characteristics: 1) the diameter of the smaller end of the fifth section 88 is within a range of about 7 mm to about 10 mm; 2) the diameter of the larger end of the fifth section 88 is within a range of about 15 mm to about 25 mm; and 3) the transition curve on each end of the fifth section 88 is defined by a radius which is within a range of about 20 mm to about 40 mm.

A sixth section 92 of the airflow conduit 68 extends from an end of the fifth section 88 toward the outlet port 94 of the airflow conduit 68. The principal function of the sixth section 92 is allow for the positioning of part of the droplet ejection cartridge housing 104 within the airflow conduit 68 and to provide for a certain airflow around that portion of the droplet ejection cartridge housing 104 which is disposed within the airflow conduit 68 and which will be described in more detail below. Again, the droplet ejection cartridge 152 is removably disposed within the droplet ejection cartridge housing 104 such that at least part thereof is also disposed within the airflow conduit 68.

A seventh section 96 of the airflow conduit 68 extends from an end of the sixth section 92 toward the outlet port 94 of the airflow conduit 68 which is defined by an end of the seventh section 96. The principal function of the seventh section 96 is to converge the "split" airflows downstream of the location where medicament is dispensed into the airflow conduit 68 by the droplet ejection cartridge 152. Generally, the seventh section 96 at least generally converges toward the reference axis 74 progressing in the direction of the outlet port 94 of the airflow conduit 68.

The above-described airflow conduit 68 defines an airflow passageway 98 through which air may be directed from the plenum 56 to the mouthpiece 200 when fluidly interconnected with the outlet port 94 of the airflow conduit 68. This airflow passageway 98 may be characterized as including a first airflow passageway section **98*a* which extends from the inlet port 70 toward the 153 droplet ejection cartridge housing 104, part of which is again disposed within the sixth section 92 of the airflow conduit 68. There the airflow passageway 98 splits into at least a second airflow passageway section 98*b* and a third airflow passageway section 98c which proceed "around" that portion of the droplet ejection cartridge housing 104 which is disposed within the airflow conduit 68 and at least generally along the reference axis 74. Both the second airflow passageway section 98*b* and third airflow passageway section 98*c* then effectively terminate at the outlet port 94 of the airflow conduit 68 where they are merged into the hollow interior of the mouthpiece 200**.

Both the second airflow passageway section **98*b* and third airflow passageway section 98*c* are defined at least in part by the spacing between a corresponding portion of the droplet ejection cartridge housing 104 and a corresponding portion of the airflow conduit 68 in its sixth section 92. In one embodiment, the "height" of each of the second airflow passageway section 98*b* and the third airflow passageway section 98*c* is within a range of about 5 mm to about 10 mm. In the illustrated embodiment the droplet ejection cartridge housing 104 is configured to further facilitate the definition of these airflow passageway sections 98*b* and 98*c***.

The droplet ejection cartridge housing 104 generally includes a top 116, a bottom 120 which is disposed opposite of this top 116, a first side 124, and a second side 128 which is disposed opposite the first side 124. Characterizing the droplet ejection cartridge 152 in this manner is not meant to limit the inhaler 2 to any particular orientation during medicament delivery operations, but is simply for purposes of providing a frame of reference. The droplet ejection cartridge housing 104 further includes a front end 132 which projects at least generally toward the outlet port 94 of the airflow conduit 68, as well as a rear end 144 which projects at least generally toward the inlet port 70 of the airflow conduit 68.

Additionally, it may be appropriate to have a pair of laterally spaced ribs 112 which may extend along at least the top 116 and the bottom 120 of the droplet ejection cartridge housing 104. These ribs 112 engage corresponding portions of the airflow conduit 68 to further define the second airflow passageway section **98*b* and the third airflow passageway section 98*c* and assist in the formation of a seal between the ejection cartridge housing 104 and the airflow conduit 68 as illustrated in FIGS. 5–6. That is, the "vertical" extent of the second airflow passageway section 98*b* is defined by the space between the airflow conduit section 68*a* and the top 116 of the droplet ejection cartridge housing 104, the "width" of the second airflow passageway section 98*b* is defined by the space between the ribs 112 disposed on the top 116 of the droplet ejection cartridge housing 104, the "vertical" extent of the third airflow passageway section 98*c* is defined by the space between the airflow conduit section 68*b* and the bottom 120 of the droplet ejection cartridge housing 104, and the "width" of the third airflow passageway section 98*c* is defined by the space between the ribs 112 disposed on the bottom 120 of the droplet ejection cartridge housing 104. Instead of forming the ribs 112 on the droplet ejection cartridge housing 104, it should be appreciated that similarly configured ribs could instead be formed on the interior of the airflow conduit 68 in its sixth section 92 so as extend toward and engage the droplet ejection cartridge housing 104. In one embodiment, the width of each of the second airflow passageway section 98b and the third airflow passageway 98c** is within a range of about 3 mm to about 6 mm.

Figure 4:
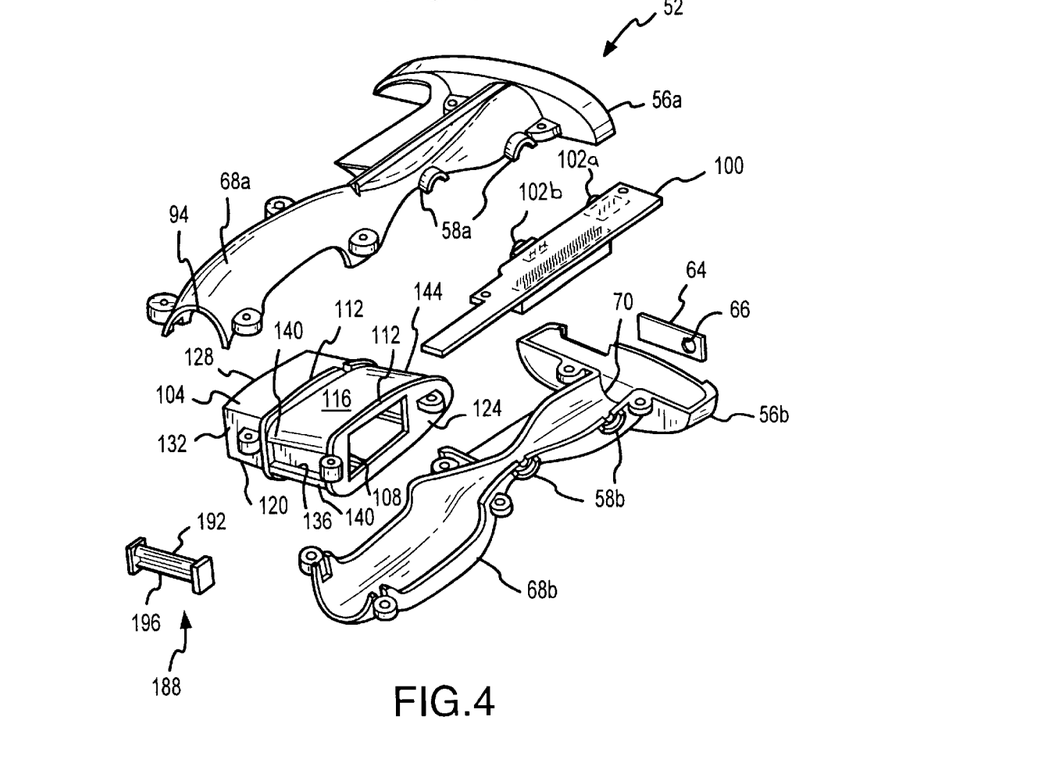
Figure 6:
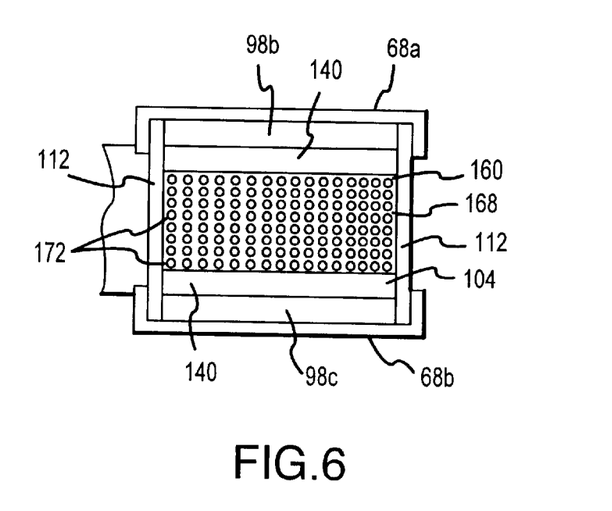
Figure 7:
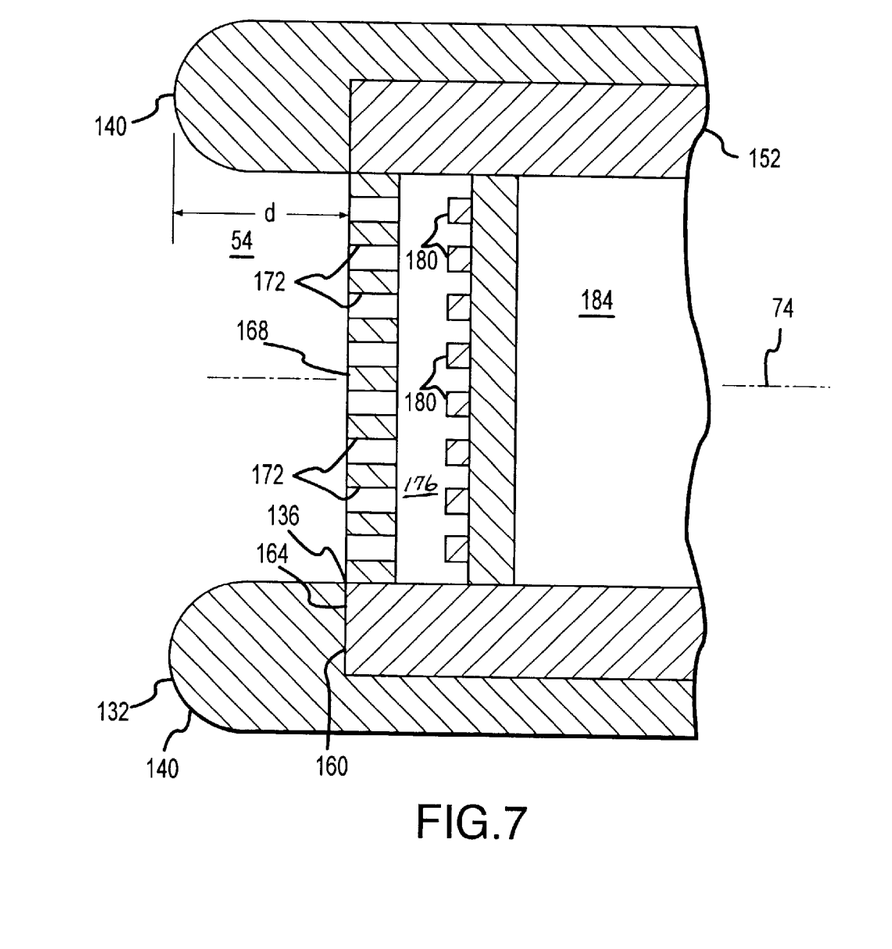
Figure 8:
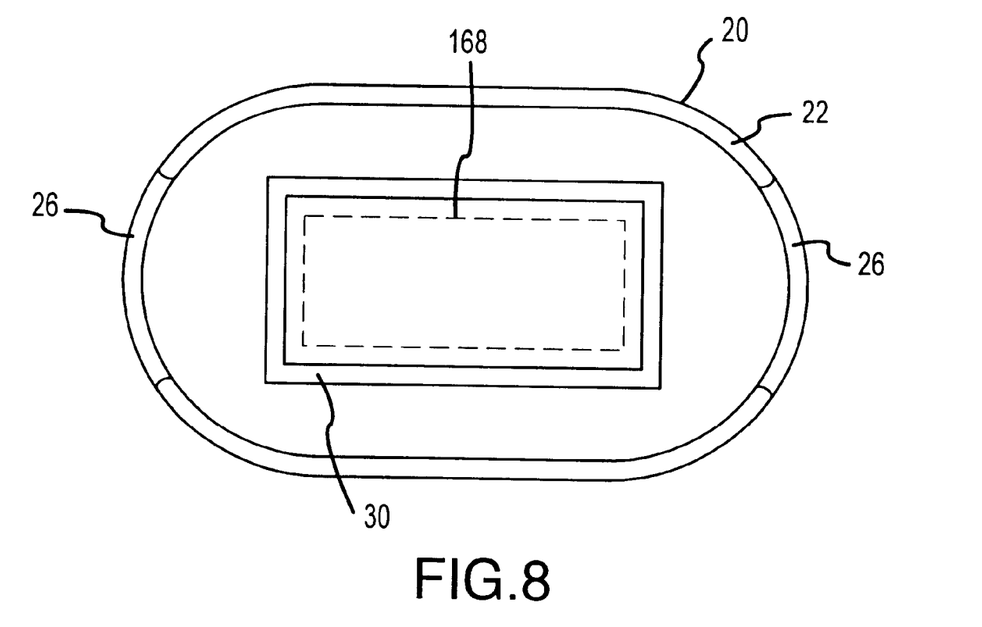

FIGS. 4 and 6 illustrate that the above-noted air passageway defining ribs 112 also extend down the front end 132 of the droplet ejection cartridge housing 104. The same ribs 112 also extend around the rear end 144 of the droplet ejection cartridge housing 104 as well. That is, the pair of spaced ribs 112 may in fact extend about the entire perimeter of the droplet ejection cartridge housing 104. Disposing the ribs 112 down the front end 132 of the droplet ejection cartridge housing 104 and disposing the ribs 112 down along the rear end 144 of the droplet ejection cartridge housing 104 provides the function of sealing the airflow conduit 68 around the droplet ejection cartridge housing 104.

The droplet ejection cartridge 152 is disposed within the droplet ejection cartridge housing 104 for purposes of dispensing medicament or the like into the airflow through the airflow conduit 68 which is generated by an inhalation of a user of the inhaler 2 at a location which is longitudinally spaced from where air initially enters the airflow conduit assembly 52 (i.e., the air inlet 60 of the plenum 56 which is longitudinally spaced from the droplet ejection cartridge 152 at a location which is "upstream" therefrom in relation to the flow through the airflow conduit assembly 52 during inhalation). Preferably, the droplet ejection cartridge 152 is removably disposed within the droplet ejection cartridge housing 104 as noted. In this regard, the droplet ejection cartridge housing 104 includes a cartridge aperture 108. This cartridge aperture 108 extends through the droplet ejection cartridge housing 104 at least generally perpendicular to the reference axis 74 and is aligned with the cartridge aperture 16 formed in the inhaler housing 6. Therefore, the cartridge access cover 18 may be removed, and the droplet ejection cartridge 152 may be both loaded into and removed from the cartridge aperture 108 within the droplet ejection cartridge housing 104 by passage through the cartridge aperture 16 formed in the inhaler housing 6 along a direction which is at least generally perpendicular to the reference axis 74.

The droplet ejection cartridge housing 104 is not totally enclosed within the airflow conduit 68, as illustrated in FIG. 4, so as to allow the droplet ejection cartridge 152 to be removable from and insertable into the droplet ejection cartridge housing 104 by a user of the inhaler 2. The above-noted ribs 112 facilitate this removability feature of the droplet ejection cartridge 152 by their definition of the second and third airflow passageway sections 98b, 98c. It should be appreciated that the airflow conduit 68 could extend down over the side 124 of the droplet ejection cartridge housing 104 without affecting this removability feature, since the cartridge aperture 108 need only be accessible on one side of the housing 104 for insertion of the droplet ejection cartridge 152 into the housing 104 (the cartridge aperture 108 extends across the entire extent of the droplet ejection cartridge housing 104 in the illustrated embodiment, although such is not required). Another airflow passageway section could then extend past the side 124 of the droplet ejection cartridge housing 104, although it is currently believed that it would still be desirable to have a defined channel for air to flow therethrough (e.g., by including ribs thereon similar to the ribs 112 noted above). However, this would provide for an asymmetrical flow about the droplet ejection cartridge housing 104. In order for an airflow passageway to pass the side 128 of the droplet ejection cartridge housing 104 to maintain a symmetrical flow about the droplet ejection cartridge housing 104 in this case, the configuration of the cover 18 would likely have to be modified such that it could interface with the airflow conduit 68 to define another air passageway section for passing an airflow along the side 128 of the droplet ejection cartridge housing 104.

Reference should now be made to FIGS. 3, 4, 6, and 7 for a more detailed discussion of the droplet ejection cartridge 152. The droplet ejection cartridge 152 generally includes a PCB interface 156 along one of its sides for interfacing with a printed circuit board 100 which controls the operation of the inhaler 2. The above-noted pressure sensors 102 are mounted on this printed circuit board 100. The droplet ejection cartridge 152 further includes a face 160. There are principally two regions on the face 160 of the droplet ejection cartridge 152. One is a nozzle region 168 which includes a plurality of droplet ejection orifices 172. Disposed on at least a portion of the perimeter of the nozzle region 168 is a circuit region 164 to allow appropriate signals to be directed to one or more resistors 180 of the droplet ejection cartridge 152 which function as the actuators for discharging medicament or the like from the droplet ejection cartridge 152. Preferably, the various resistors 180 are independently operable or actuatable to direct medicament out of selected droplet ejection orifices 172. That is, each droplet ejection orifice 172 has its own resistor 180 such that there is a one-to-one relationship between the droplet ejection orifices 172 and the resistors 180, and such that medicament may be directed out of any combination of droplet ejection orifices 172 by activation of the appropriate resistor 180.

The resistors 180 are disposed in spaced relation to their corresponding droplet ejection orifice 172 by a medicament cavity 176 which is at least fluidly interconnectable with a medicament reservoir 184 within the droplet ejection cartridge 152 (illustrated by the dashed line in FIG. 7). Generally, medicament is directed from the medicament reservoir 184 into the medicament cavity 176. Activation of a particular resistor 180, via an electrical signal from the printed circuit board 100 which is transferred to the resistor 180 along an appropriate line or lead on the PCB interface 156 and/or circuit region 164, increases the temperature of the subject resistor 180. This increase in temperature of the resistor 180 causes a bubble to develop within the medicament within the medicament cavity 176 in proximity to the "activated" resistor 180. Enlargement of this bubble by the continued application of the signal to the subject resistor 180 directs medicament out through the droplet ejection orifice 172 which is aligned with the "activated" resistor 180.

A number of features of the inhaler 2 are directed toward the manner in which droplets of medicament are introduced into the airflow through the airflow passageway 98 by the droplet ejection cartridge 152. Initially, the droplet ejection cartridge housing 104 includes an ejection aperture 136 on its front end 132 which projects at least generally toward the outlet port 94 of the airflow conduit 68. This ejection aperture 136 is actually recessed on the front end 132 by a pair of vertically-spaced projections 140 on the upper and lower extreme of the droplet ejection cartridge housing 104. Each of these projections 140 extend at least generally in the direction of the outlet port 94 of the airflow conduit 68. One of the projections 140 defines a boundary of sorts for the second airflow passageway section **98*b*, while the other of these projections 140 defines the boundary of sorts for the third airflow passageway section 98*c***.

At least part of a droplet ejection zone 54 is defined between the pair of spaced projections 140. Stated another way, the region within the airflow conduit 68 where droplets of medicament are initially introduced by the droplet ejection cartridge 152 is effectively out of or outside any airflow through the airflow conduit 68 which is generated by a user of the inhaler 2 during an inhalation.

Therefore, the velocity within the droplet ejection zone 54 between the projections 140 is at least substantially less than the velocity of the airflow through the second airflow passageway section 98*b* and/or the third airflow section passageway 98*c*, and is believed to be at substantially a low velocity (e.g., in one embodiment such that a ratio of the velocity of the airflow through either of the airflow passageway section 98*b* or 98*c*, to the velocity in the zone droplet ejection 54, is less than about one-tenth). In one embodiment, the distance "$d_1$" from the forward portion of these projections 140 to the droplet ejection orifices, which thereby defines at least part of the length of the droplet ejection zone 54 and measured along the reference axis 74, is less than about 10 mm, but is at least about 0.1 mm.

The low velocity droplet ejection zone 54 may be extended by a vane assembly 188 which is illustrated in FIGS. 4–5. The vane assembly 188 generally includes an upper vane 192 and a lower vane 196 which is disposed in spaced relation thereto. The vane assembly 188 preferably detachably interconnects with the droplet ejection cartridge housing 104 so as to dispose the upper vane 192 and lower vane 196 in the position illustrated in FIG. 5. In this regard, the upper vane 192 and lower vane 196 are least generally spaced apart by the same distance as the projections 140.

A small longitudinally extending space "$d_2$" may exist between the vanes 192, 194 and their corresponding projection 140 on the droplet ejection cartridge housing 104. This space $d_2$ provides the function of encouraging mixing of the outer flow and the medicament "cloud".

Air inhaled by the user of the inhaler 2 is directed from the plenum 56, through airflow conduit 68, and into the mouthpiece 200 when an inlet end 204 thereof is disposed in abutting engagement the outlet port 94 of the airflow conduit. This airflow is then directed into the mouth of a user of the inhaler 2 through an outlet end 208 of the mouthpiece 200. The cross-sectional profile of the mouthpiece 200 is configured to further facilitate the delivery of medicament droplets entrained in the airflow through the inhaler 2. In this regard and as illustrated in FIGS. 3 and 6, the nozzle region 168 of the droplet ejection cartridge is at least substantially rectangular in the illustrated embodiment. An elliptical profile has been selected for the mouthpiece 200 and is oriented such that it at least generally follows the perimeter of the nozzle region 168. Moreover, the cross-sectional area of the inlet end 204 of the mouthpiece 200, within a plane that is perpendicular to the reference axis 74, is greater than the cross-sectional area of the outlet end 208 of the mouthpiece 200, also within a plane that is perpendicular to the reference axis 74. In one embodiment, the ratio of this area of the inlet end 204 of the mouthpiece 200 to this area of the outlet end 208 of the mouthpiece 200 is at least about 1.5:1. In one embodiment, the inlet end 204 of the mouthpiece 200 has a circular cross-sectional profile.

The length of the mouthpiece 200 has an effect on the delivery of medicament to the user during inhalation. In one embodiment, the length of the mouthpiece 200 is selected such that medicament that is ejected from the droplet ejection cartridge 152 is traveling at least at substantially the same, and more preferably the same, velocity as the airflow prior to exiting the outlet end 208 of the mouthpiece 200 (e.g., the airflow and medicament droplets are both traveling at preferably the same velocity when exiting the outlet end 208). In this regard and in one embodiment, the distance between the face 160 of the droplet ejection cartridge 152 and the outlet end 208 of the mouthpiece 200 is at least about 20 mm for medicament which is ejected into the airflow conduit 168 at an initial velocity of about 10 m/second.

The mouthpiece 200 is again preferably detachably interconnected with the airflow conduit assembly 52. Removal of the mouthpiece 200 not only provides the above-noted possible advantages, but it also allows for an encapsulation of sorts of the nozzle region 168 of the droplet ejection cartridge 152. In this regarded and as noted above, the inhaler 2 includes a discharge ejection orifice cover 20. Referring to FIGS. 2, 3, and 8, this cover 20 generally includes a rim 22 with a pair of snap-lock members 26 which detachably interconnect the cover 20 with the inhaler housing 106 at the exit aperture 42. The cover 20 further includes a generally rectangularly-shaped seal 30 which is sized so as to be disposed about the entirety of the perimeter of the nozzle region 168 on the face 160 of the droplet ejection cartridge 152 and in engagement with the face 160.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. An inhaler, comprising:

an inhaler housing which comprises a first droplet ejection cartridge aperture;

at least one airflow passageway which comprises a first air inlet port and which is interconnected with said inhaler housing;

a droplet ejection cartridge housing which is interconnected with said inhaler housing, wherein each said airflow passageway is directed around said droplet ejection cartridge housing, wherein said droplet ejection cartridge housing comprises a second droplet ejection cartridge aperture which is aligned with said first droplet ejection cartridge aperture of said inhaler housing, and wherein said droplet ejection cartridge housing further comprises a droplet ejection aperture;

a droplet ejection cartridge which is removably disposed within said second droplet ejection cartridge aperture of said droplet ejection cartridge housing by passage through said first droplet ejection cartridge aperture of said inhaler housing, wherein said droplet ejection cartridge comprises a medicament reservoir, a plurality of droplet ejection orifices which are at least fluidly interconnectable with said medicament reservoir and which are oriented to direct medicament droplets through said droplet ejection aperture of said droplet ejection cartridge housing, and at least one droplet ejection actuator; and a mouthpiece which is at least fluidly interconnectable with said at least one airflow passageway and which comprises a first outlet end which may be inserted into a mouth of a user of said inhaler.

2. An inhaler, as claimed in claim 1, further comprising:

a cover for said first droplet ejection cartridge aperture of said inhaler housing.

3. An inhaler, as claimed in claim 2, wherein:

said cover is movably interconnected with said inhaler housing.

4. An inhaler, as claimed in claim 2, wherein:

said cover is totally removable from said inhaler housing.

5. An inhaler, as claimed in claim 1, further comprising:

an airflow conduit assembly which is interconnected with said inhaler housing, wherein each said airflow passageway extends through said airflow conduit assembly, and wherein an inlet end of said mouthpiece is at least fluidly interconnectable with said airflow conduit assembly.

6. An inhaler, as claimed in claim 5, wherein:

at least part of said droplet ejection cartridge housing is disposed within said airflow conduit assembly, and wherein at least part of said droplet ejection cartridge housing is disposed in spaced relation to said airflow conduit assembly to define part of said at least one airflow passageway.

7. An inhaler, as claimed in claim 5, wherein:

at least part of said droplet ejection cartridge housing is disposed within said airflow conduit assembly, wherein said inhaler further comprises at least one pair of spaced partitions which extend between an interior surface of said airflow conduit assembly and part of an exterior of said droplet ejection cartridge housing which is disposed within said airflow conduit assembly to define a longitudinal segment of said at least one airflow passageway.

8. An inhaler, as claimed in claim 5, wherein:

said airflow conduit assembly comprises a first section, wherein said first section is divergent when progressing in a direction which is at least generally toward said first air inlet port and away from said mouthpiece when interconnected with said airflow conduit assembly, and wherein said first section terminates at said first air inlet port.

9. An inhaler, as claimed in claim 8, wherein:

a wall of said airflow conduit assembly which defines said first section is at least generally accurately-shaped relative to a reference axis which defines a longitudinal extent of said airflow conduit assembly.

10. An inhaler, as claimed in claim 8, wherein:

said airflow conduit assembly further comprises a plenum, wherein said first air inlet port fluidly interconnects said plenum and said first section, with said first section thereby being disposed between said plenum and said mouthpiece when interconnected with said airflow conduit assembly, and wherein said plenum comprises a second air inlet port through which air may be drawn into said plenum and directed into said first section of said airflow conduit assembly for provision to said mouthpiece when interconnected with said airflow conduit assembly.

11. An inhaler, as claimed in claim 5, wherein:

said airflow conduit assembly comprises a plenum and an airflow conduit, wherein said first air inlet port fluidly interconnects said plenum and said airflow conduit, wherein said mouthpiece is fluidly interconnectable with an end of said airflow conduit which is opposite that which defines said first air inlet port, and wherein said plenum comprises a second air inlet port through which air may be drawn into said plenum and directed into said airflow conduit through said first air inlet port for provision to said mouthpiece when interconnected with said airflow conduit assembly.

12. An inhaler, as claimed in claim 11, wherein:

an interior volume of said plenum is at least about 9,000 $mm^3$.

13. An inhaler, as claimed in claim 11, further comprising:

means for changing a size of said second air inlet port.

14. An inhaler, as claimed in claim 11, wherein:

said first and second air inlet ports are offset.

15. An inhaler, as claimed in claim 5, wherein:

said airflow conduit assembly is defined by a first diameter at a first location, wherein said airflow conduit assembly is defined by a second diameter at a second location which is spaced from said first location at least generally in a direction of said mouthpiece when interconnected with said airflow conduit assembly, wherein said airflow conduit assembly is defined by a third diameter at a third location which is spaced from said second location at least generally in a direction of said mouthpiece when interconnected with said airflow conduit assembly, wherein said first diameter is greater than said second diameter, wherein said third diameter is greater than each of said first and second diameters, wherein said droplet ejection cartridge housing is disposed within a portion of said airflow conduit assembly which is defined by said third diameter, wherein said inlet end of said mouthpiece is disposed opposite said first outlet end of said mouthpiece, wherein said inlet end of said mouthpiece interfaces with said airflow conduit assembly when interconnected with said airflow conduit assembly, and wherein a size of said inlet end of said mouthpiece is greater than a size of said first outlet end of said mouthpiece.

16. An inhaler, as claimed in claim 5, wherein:

said droplet ejection cartridge housing comprises first, second, third, and fourth sides, wherein said first and second sides are disposed opposite of each other, wherein said third and fourth sides are disposed opposite of each other, wherein a first space between said first side of said droplet ejection device housing and an interior surface of said airflow conduit assembly defines a first airflow passageway, and wherein a second space between said second side of said droplet ejection device housing and said airflow conduit assembly defines a second airflow passageway, and wherein said at least one air passageway comprises said first and second air passageways.

17. An inhaler, as claimed in claim 16, wherein:

each said airflow passageway extends past said droplet ejection cartridge housing other than between said third side of said droplet ejection cartridge housing and said airflow conduit assembly and other than between said fourth side of said droplet ejection cartridge housing and said airflow conduit assembly.

18. An inhaler, as claimed in claim 16, further comprising:

a first pair of laterally spaced partitions which extend between said first side of said droplet ejection cartridge housing and said interior surface of said airflow conduit assembly, wherein said first air passageway is defined between said first pair of laterally spaced partitions; and a second pair of laterally spaced partitions which extend between said second side of said droplet ejection cartridge housing and said interior surface of said airflow conduit assembly, wherein said second air passageway is defined between said second pair of laterally spaced partitions.

19. An inhaler, as claimed in claim 17, wherein:

said second droplet ejection cartridge aperture extends through said droplet ejection cartridge housing at least substantially perpendicularly to a reference axis associated with a longitudinal extent of said airflow conduit assembly.

20. An inhaler, as claimed in claim 17, wherein:

said droplet ejection cartridge housing comprises a first end which projects at least generally toward said mouthpiece when interconnected with said airflow conduit assembly, wherein said first end comprises a recess, wherein said droplet ejection aperture is disposed on said recess, and wherein a depth of said recess, measured in a direction which is parallel with a central reference axis associated with a longitudinal extent of said airflow conduit assembly, is at least about 0.1 mm.

21. An inhaler, as claimed in claim 1, wherein:

said droplet ejection cartridge housing comprises a first end which projects at least generally toward said mouthpiece when interconnected with said at least one airflow passageway, wherein said first end comprises a recess, and wherein said droplet ejection aperture is disposed on said recess.

22. An inhaler, as claimed in claim 1, wherein:

said droplet ejection cartridge housing comprises a first end which projects at least generally toward said mouthpiece when interconnected with said at least one airflow passageway, wherein said inhaler further comprises a pair of spaced apart vanes which are attached to said first end of said droplet ejection cartridge housing, wherein said plurality of droplet ejection orifices are directed to eject medicament droplets between said pair of spaced vanes, and wherein each said airflow passageway passes said pair of spaced vanes on a side of said vanes which is opposite that which interfaces with said medicament droplets ejected through said plurality of droplet ejection orifices.

23. An inhaler, as claimed in claim 1, wherein:

said mouthpiece is detachably interconnectable with said inhaler at each of first and second locations which are disposed in spaced relation, wherein said mouthpiece is fluidly interconnected with said at least one airflow passageway when said mouthpiece is interconnected with said inhaler at said first location whereby having said mouthpiece interconnected with said inhaler at said first location provides for medicament delivery operations, wherein said mouthpiece is fluidly disconnected from said at least one airflow passageway when said mouthpiece is interconnected with said inhaler at said second location whereby having said mouthpiece interconnected with said inhaler at said second location provides for storage of said mouthpiece between uses of said inhaler for medicament delivery operations.

24. An inhaler, as claimed in claim 1, wherein:

said mouthpiece is detachably interconnected with said at least one airflow passageway, wherein said mouthpiece may be disconnected from said at least one air passageway, and wherein said inhaler further comprises an airflow passageway cover for said at least one airflow passageway when said mouthpiece is disconnected from said at least one airflow passageway.

25. An inhaler, as claimed in claim 24, wherein:

said airflow passageway cover further comprises a seal which interfaces with a face of said droplet ejection cartridge which has said plurality of droplet ejection orifices and which is disposed about an entirety of a perimeter of said plurality of droplet ejection orifices.

26. An inhaler, as claimed in claim 24, further comprising:

a tether which interconnects said inhaler housing and said airflow passageway cover.

27. An inhaler, comprising:

an inhaler housing;

at least one airflow passageway which comprises a first air inlet port and which is interconnected with said inhaler housing;

a medicament container which is interconnected with said inhaler housing;

a droplet ejection device which is interconnected with said inhaler housing and which is at least fluidly interconnectable with said medicament container;

a mouthpiece which is detachably interconnectable with said inhaler at each of first and second locations which are disposed in spaced relation by a total removal of said mouthpiece from said inhaler, wherein said mouthpiece is fluidly interconnected with said at least one airflow passageway when said mouthpiece is interconnected with said inhaler at said first location whereby having said mouthpiece interconnected with said inhaler at said first location provides for medicament delivery operations, wherein said mouthpiece is fluidly disconnected from said at least one airflow passageway when said mouthpiece is interconnected with said inhaler at said second location whereby having said mouthpiece interconnected with said inhaler at said second location provides for storage of said mouthpiece between adjacent-in-time said medicament delivery operations.

28. An inhaler, as claimed in claim 27, wherein:

said inhaler housing comprises a first droplet ejection cartridge aperture;

said inhaler further comprises a droplet ejection cartridge housing which is interconnected with said inhaler housing, wherein each said airflow passageway is directed around said droplet ejection cartridge housing, wherein said droplet ejection cartridge housing comprises a second droplet ejection cartridge aperture which is aligned with said first droplet ejection cartridge aperture of said inhaler housing, and wherein said droplet ejection cartridge housing further comprises a droplet ejection aperture; and said droplet ejection device comprises a droplet ejection cartridge which is removably disposed within said second droplet ejection cartridge aperture of said droplet ejection cartridge housing by passage through said first droplet ejection cartridge aperture of said inhaler housing, wherein said droplet ejection cartridge comprises a medicament reservoir, a plurality of droplet ejection orifices which are at least fluidly interconnectable with said medicament reservoir and which are oriented to direct medicament droplets through said droplet ejection aperture of said droplet ejection cartridge housing, and at least one droplet ejection actuator.

29. An inhaler, as claimed in claim 27, further comprising:

an airflow conduit assembly which is interconnected with said inhaler housing, wherein each said airflow passageway extends through said airflow conduit assembly, and wherein an inlet end of said mouthpiece is fluidly interconnectable with said airflow conduit assembly.

30. An inhaler, as claimed in claim 29, wherein:

said airflow conduit assembly comprises a first section, wherein said first section is divergent when progressing in a direction which is at least generally toward said first air inlet port and away from said mouthpiece when interconnected with said airflow conduit assembly, and wherein said first section terminates at said first air inlet port.

31. An inhaler, as claimed in claim 30, wherein:

a wall of said airflow conduit assembly which defines said first section is at least generally accurately-shaped relative to a reference axis which defines a longitudinal extent of said airflow conduit assembly.

32. An inhaler, as claimed in claim 30, wherein:

said airflow conduit assembly further comprises a plenum, wherein said first air inlet port fluidly interconnects said plenum and said first section, with said first section thereby being disposed between said plenum and said mouthpiece when interconnected with said airflow conduit assembly, and wherein said plenum comprises a second air inlet port through which air may be drawn into said plenum and directed into said first section of said conduit assembly for provision to said mouthpiece when interconnected with said airflow conduit assembly.

33. An inhaler, as claimed in claim 29, wherein:

said airflow conduit assembly comprises a plenum and an airflow conduit, wherein said first air inlet port fluidly interconnects said plenum and said airflow conduit, wherein said mouthpiece is fluidly interconnectable with an end of said airflow conduit which is opposite that which defines said first air inlet port, and wherein said plenum comprises a second air inlet port through which air may be drawn into said plenum and directed into said airflow conduit through said first air inlet port for provision to said mouthpiece when interconnected with said airflow conduit assembly.

34. An inhaler, as claimed in claim 33, wherein:

an interior volume of said plenum is at least about 9,000 mm$^3$.

35. An inhaler, as claimed in claim 33, further comprising:

means for changing a size of said second air inlet port.

36. An inhaler, as claimed in claim 33, wherein:

said first and second air inlet ports are offset.

37. An inhaler, as claimed in claim 29, wherein:

said airflow conduit assembly is defined by a first diameter at a first location, wherein said airflow conduit assembly is defined by a second diameter at a second location which is spaced from said first location at least generally in a direction of said mouthpiece when interconnected with said airflow conduit assembly, wherein said airflow conduit assembly is defined by a third diameter at a third location which is spaced from said second location at least generally in a direction of said mouthpiece when interconnected with said airflow conduit assembly, wherein said first diameter is greater than said second diameter, and wherein said third diameter is greater than each of said first and second diameters.

38. An inhaler, as claimed in claim 37, wherein:

said inlet end of said mouthpiece is disposed opposite an outlet end of said mouthpiece, and wherein a size of said inlet end of said mouthpiece is greater than a size of said outlet end of said mouthpiece.

39. An inhaler, as claimed in claim 27, further comprising:

an airflow passageway cover for said at least one airflow passageway when said mouthpiece is disconnected from said at least one airflow passageway.

40. An inhaler, as claimed in claim 39, further comprising:

a tether which interconnects said inhaler housing and said airflow passageway cover.

41. An inhaler, comprising:

a plenum which comprises a first air inlet port, wherein an interior volume of said plenum is at least about 9,000 mm$^3$;

an airflow conduit which is fluidly interconnected with said plenum and which comprises first and second longitudinally spaced ends, wherein said first end interfaces with said plenum, and wherein said first end of said airflow conduit is offset from said first air inlet port;

a droplet ejection device which is at least fluidly interconnectable with said airflow conduit, wherein said droplet ejection device comprises a medicament reservoir, a plurality of droplet ejection orifices which are at least fluidly interconnectable with said medicament reservoir, and at least one droplet ejection actuator; and mouthpiece which is at least interconnectable with said second end of said airflow conduit.

42. An inhaler, as claimed in claim 41, further comprising:

an inhaler housing which comprises a first droplet ejection cartridge aperture; and a droplet ejection cartridge housing which is interconnected with said inhaler housing, wherein said airflow conduit comprises at least one airflow passageway, wherein each said airflow passageway is directed around said droplet ejection cartridge housing, wherein said droplet election cartridge housing comprises a second droplet ejection cartridge aperture which is aligned with said first droplet election cartridge aperture of said inhaler housing, wherein said droplet ejection cartridge housing further comprises a droplet ejection aperture, and wherein said droplet ejection device comprises a droplet ejection cartridge which is removably disposed within said second droplet ejection cartridge aperture of said droplet ejection cartridge housing by passage through said first droplet ejection cartridge aperture of said inhaler housing.

43. An inhaler, as claimed in claim 41, wherein:

said airflow conduit comprises a first section, wherein said first section is divergent when progressing in a direction which is at least generally toward said first air inlet port and away from said mouthpiece when interconnected with said airflow conduit, and wherein said first section terminates at said first end.

44. An inhaler, as claimed in claim 43, wherein:

a wall of said airflow conduit which defines said first section is at least generally accurately-shaped relative to a reference axis which defines a longitudinal extent of said airflow conduit.

45. An inhaler, as claimed in claim 41, wherein:

first air inlet port is located on a surface of said plenum that projects toward said airflow conduit.

46. An inhaler, as claimed in claim 41, further comprising:

means for changing a size of said first air inlet port.

47. An inhaler, as claimed in claim 41, wherein:

said airflow conduit is defined by a first diameter at a first location, wherein said airflow conduit is defined by a second diameter at a second location which is spaced from said first location at least generally in a direction of said mouthpiece when interconnected with said airflow conduit, wherein said airflow conduit is defined by a third diameter at a third location which is spaced from said second location at least generally in a direction of said mouthpiece when interconnected with said airflow conduit, wherein said first diameter is greater than said second diameter, and wherein said third diameter is greater than each of said first and second diameters.

48. An inhaler, as claimed in claim 41, wherein:

said mouthpiece comprises an inlet end and an outlet end which may be inserted into a mouth of a user of said inhaler, wherein said inlet end of said mouthpiece interfaces with said airflow conduit when said mouthpiece is interconnected with said airflow conduit, and wherein a size of said inlet end of said mouthpiece is greater than a size of said outlet end of said mouthpiece.

49. An inhaler, as claimed in claim 41, wherein:

said mouthpiece is detachably interconnectable with said inhaler at each of first and second locations which are disposed in spaced relation, wherein said mouthpiece is fluidly interconnected with said airflow conduit when said mouthpiece is interconnected with said inhaler at said first location whereby having said mouthpiece interconnected with said inhaler at said first location provides for medicament delivery operations, and wherein said mouthpiece is fluidly disconnected from said airflow conduit when said mouthpiece is interconnected with said inhaler at said second location whereby having said mouthpiece interconnected with said inhaler at said second location provides for storage of said mouthpiece between uses of said inhaler for medicament delivery operations.

50. An inhaler, as claimed in claim 49, further comprising:

an airflow passageway cover for said at least one airflow passageway when said mouthpiece is disconnected from said airflow conduit.

51. An inhaler, as claimed in claim 50, further comprising:

a tether which interconnects said inhaler housing and said airflow passageway cover.

52. An inhaler, comprising:

an airflow conduit assembly which comprises a first air inlet and a first air outlet and at least one airflow passageway which extends between said first air inlet and said first air outlet;

a droplet ejection cartridge housing which comprises first, second, third, and fourth sides, wherein said first and second sides are disposed opposite of each other, wherein said third and fourth sides are disposed opposite of each other, wherein at least part of said droplet ejection cartridge housing is disposed within said airflow conduit assembly, wherein a first space between said first side of said droplet ejection device housing and an interior surface of said airflow conduit assembly defines a first airflow passageway, wherein a second space between said second side of said droplet ejection device housing and said interior surface of said airflow conduit assembly defines a second airflow passageway, wherein said at least one airflow passageway comprises said first and second airflow passageways, and wherein each said airflow passageway extends past said droplet ejection cartridge housing other than between said third side of said droplet ejection cartridge housing and said interior surface of said airflow conduit assembly and other than between said fourth side of said droplet ejection cartridge housing and said interior surface of said airflow conduit assembly;

a droplet ejection cartridge disposed within said droplet ejection cartridge housing, wherein said droplet ejection cartridge comprises a medicament reservoir, a plurality of droplet ejection orifices which are at least fluidly interconnectable with said medicament reservoir, and at least one droplet ejection actuator; and a mouthpiece which is at least fluidly interconnectable with said first outlet port of said airflow conduit assembly.

* * * * *

UNITED STATES PATENT AND TRADEMARK OFFICE
CERTIFICATE OF CORRECTION

PATENT NO.     : 6,629,524 B1
DATED          : October 7, 2003
INVENTOR(S)    : Goodall et al.

It is certified that error appears in the above-identified patent and that said Letters Patent is hereby corrected as shown below:

Column 9,
Line 67, delete the word "upperplenum", and insert therefor -- upper plenum --.

Column 17,
Lines 28 and 29, delete the word "sp aced", and insert therefore -- spaced --.
Line 45, delete the word "accurately-shaped", and insert therefore
-- arcuately-shaped --.

Column 21,
Line 15, delete the word "accurately-shaped", and insert therefore
-- arcuately-shaped --.

Column 22,
Line 57, delete the word "accurately-shaped", and insert therefore
-- arcuately-shaped --.

Signed and Sealed this

Second Day of December, 2003

JAMES E. ROGAN
*Director of the United States Patent and Trademark Office*